United States Patent [19]

Rubin et al.

[11] 4,191,845

[45] Mar. 4, 1980

[54] PROCESS FOR CONVERTING UNSATURATED C4 HYDROCARBONS INTO NORMAL BUTANE

[75] Inventors: Jacob N. Rubin, Newton Highlands; Frederick B. Seufert, Arlington, both of Mass.

[73] Assignee: Stone & Webster Engineering Corporation, Boston, Mass.

[21] Appl. No.: 927,919

[22] Filed: Jul. 25, 1978

Related U.S. Application Data

[63] Continuation-in-part of Ser. No. 896,460, Apr. 14, 1978, abandoned.

[51] Int. Cl.² ............................ C07C 5/04; C07C 5/28; C07C 3/30
[52] U.S. Cl. .................................... 585/253; 585/251; 585/650; 585/324; 585/276; 585/737; 585/738; 585/741; 585/750
[58] Field of Search ......................... 260/683 R, 683.9; 268/67; 585/253, 251, 650, 324

[56] References Cited

U.S. PATENT DOCUMENTS

| | | | |
|---|---|---|---|
| 2,950,240 | 8/1960 | Weisz | 260/683 R |
| 3,751,514 | 8/1973 | Hoppstock et al. | 260/683 R |
| 3,761,538 | 9/1973 | Espino et al. | 260/683 R |

OTHER PUBLICATIONS

Asimger, *Mono–Olefins Chemistry & Technology*, Pergammon Press (1968).

*Primary Examiner*—George Crasanakis
*Attorney, Agent, or Firm*—Morgan, Finnegan, Pine, Foley & Lee

[57] ABSTRACT

Unsaturated C4 hydrocarbons are converted into normal butane by introducing an unsaturated C4 hydrocarbon stream into a hydrogenation zone to convert it into a stream of normal butane and isobutane. Normal butane is recovered from a separation zone while isobutane is directed to an isomerization zone wherein a portion of the isobutane is converted into normal butane. The stream from the isomerization zone is returned to the separation zone to recover the normal butane produced in the isomerization reaction. The normal butane produced by the process is subsequently utilized in a cracking zone to produce ethylene.

36 Claims, 6 Drawing Figures

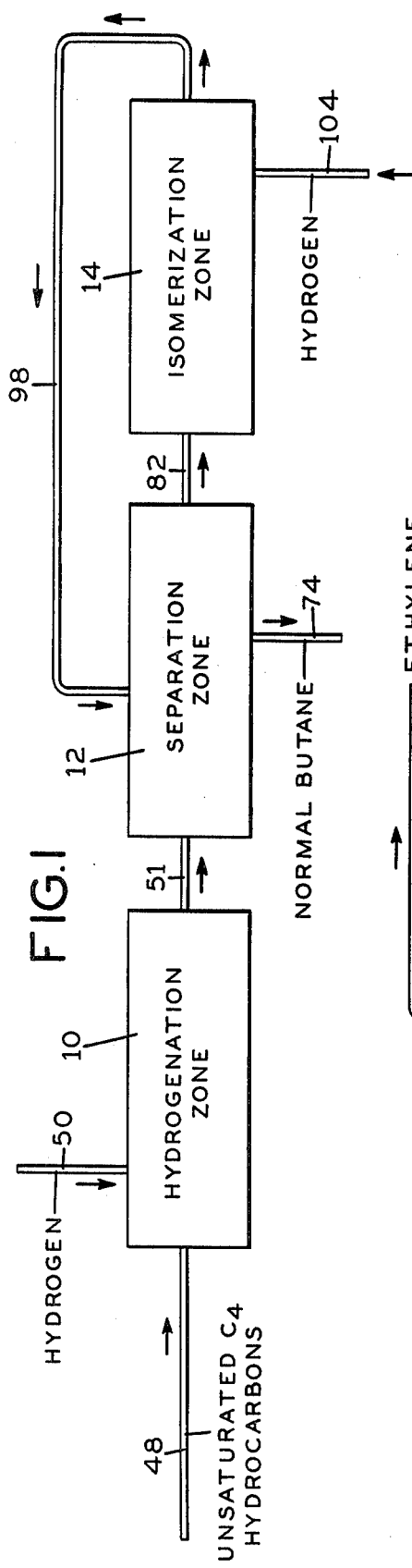
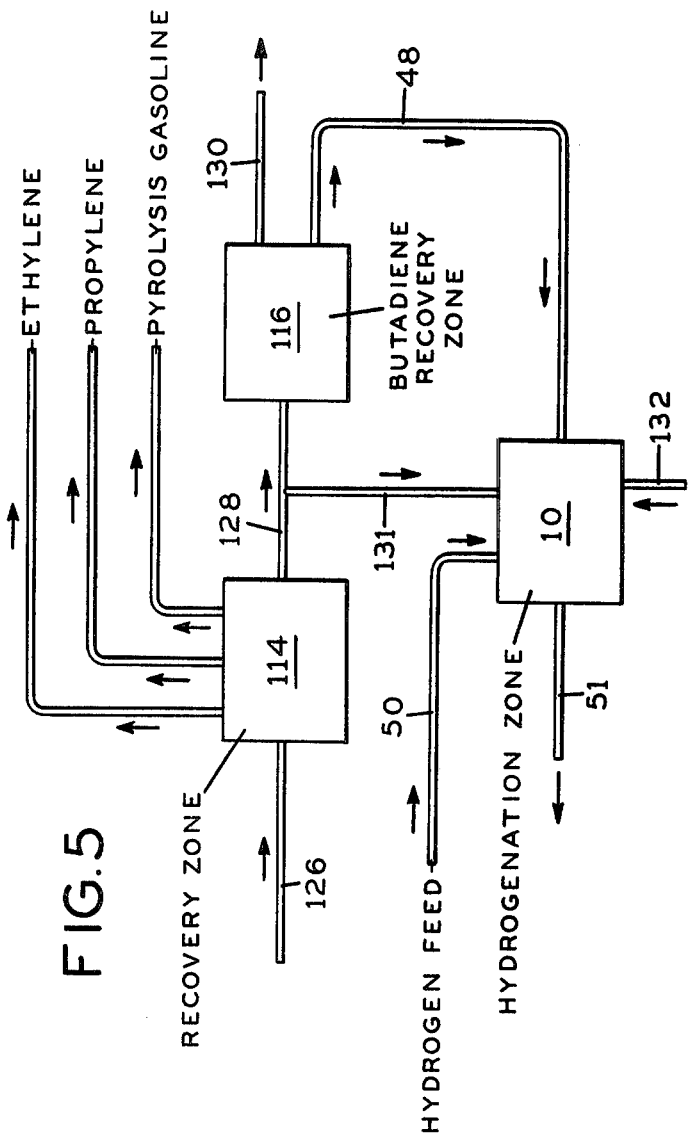

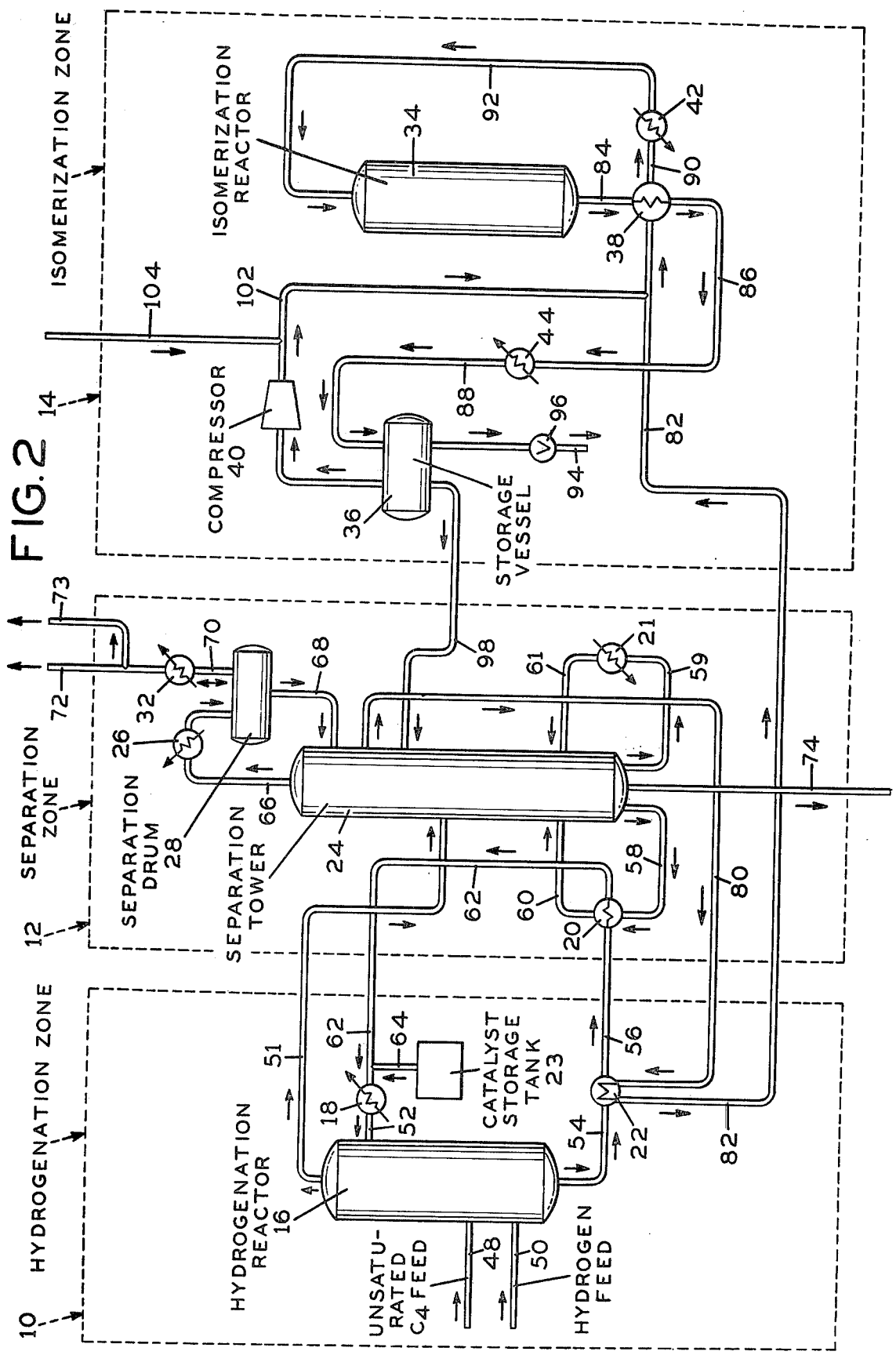

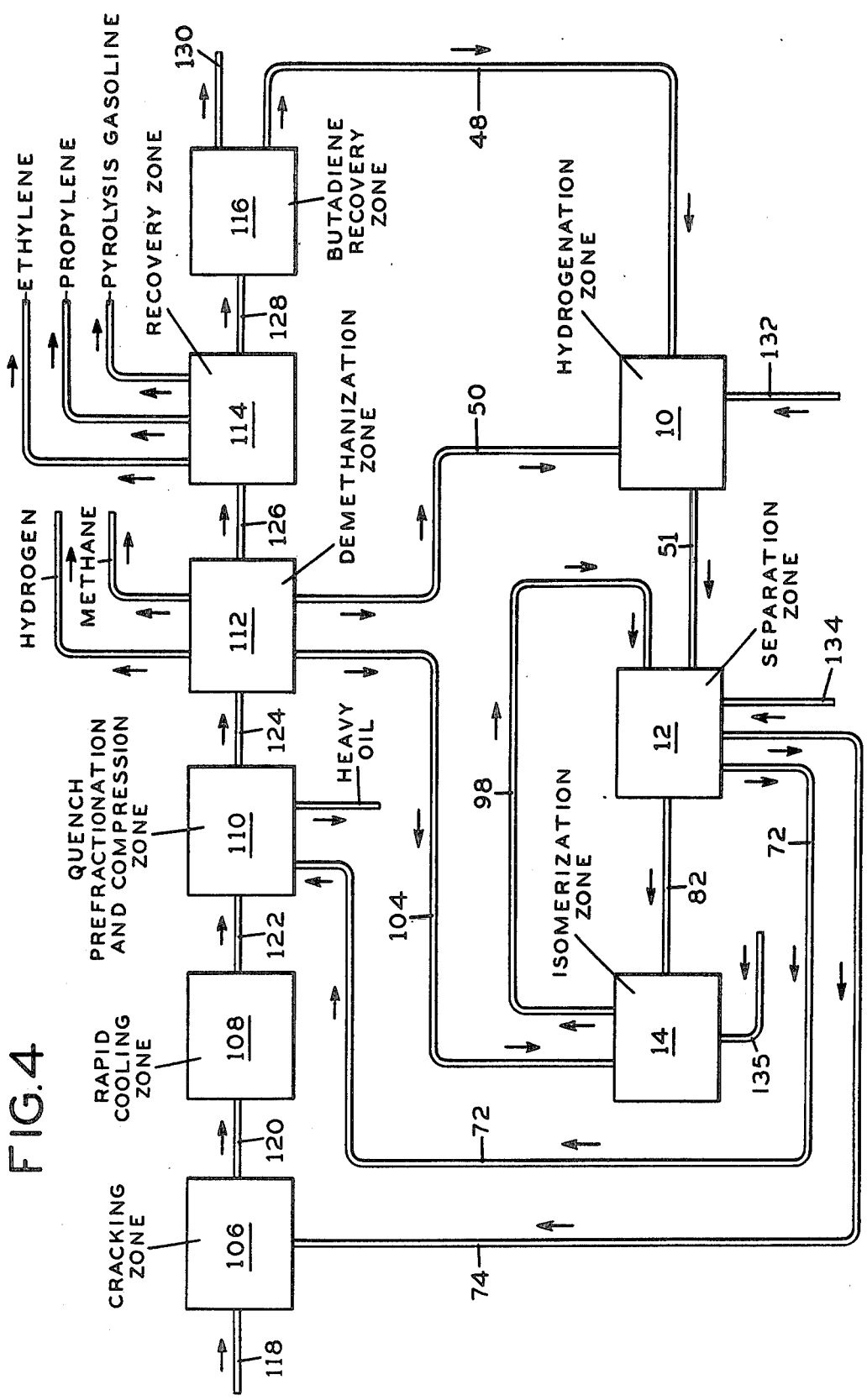

PROCESS FOR CONVERTING UNSATURATED C₄ HYDROCARBONS INTO NORMAL BUTANE

CROSS REFERENCE TO RELATED APPLICATIONS

This is a continuation-in-part of application Ser. No. 896,460, filed Apr. 14, 1978 and now abandoned.

FIELD OF THE INVENTION

The present invention relates to the conversion of unsaturated $C_4$ hydrocarbons into normal butane and more particularly to the conversion of normal butenes and isobutene into normal butane.

In another aspect, the invention relates to the conversion of unsaturated $C_4$ hydrocarbons generated in the recovery zone of a conventional ethylene production facility into valuable normal butane. The normal butane can thereafter be either recovered, or advantageously, recycled to the ethylene process as a premium cracking feedstock to increase the overall yield of ethylene.

BACKGROUND OF THE INVENTION

As is well known in the art, the production of ethylene by the pyrolytic cracking of hydrocarbons normally involves a series of treatment steps which can be generally described in the following manner. A hydrocarbon feedstock such as gas oil or naphtha is introduced into a high severity cracking furnace which operates at elevated temperatures, e.g., temperatures in excess of about 1500° F., wherein the feedstock is converted into ethylene, propylene, aromatic hydrocarbons, unsaturated $C_4$ hydrocarbons and a variety of other products. The product stream of gases (ethylene, etc.) emanating from the cracking furnace is thereafter directed through cooling means wherein the temperature of the gases is rapidly reduced. The cooled gas stream is thereafter introduced into quench prefractionation equipment for further cooling and the removal of a heavy hydrocarbon fraction from the cracked gas stream. The cracked gases are thereafter introduced into a compression zone (frequently comprising a series of four compression stages) whereby the pressure of the gas stream is increased to the pressure necessary for achieving the desired product recoveries in the product recovery zone. The pressurized cracked gas stream leaving the compression zone is then introduced into a demethanization zone to separate hydrogen and methane from the pressurized gas stream. The remainder of the pressurized gas stream is thereafter directed through a recovery zone for recovery of ethylene product from other products in the pressurized cracked gas stream.

In general, the recovery zone includes a series of fractional distillation towers which are adapted to separate the pressurized cracked gas stream into a stream of ethylene, and also streams of by-products such as propylene, crude unsaturated $C_4$ hydrocarbons, raw pyrolysis gasoline, etc.

The crude unsaturated $C_4$ hydrocarbon by-product stream separated in the recovery zone is usually directed to a butadiene recovery facility where high purity 1,3-butadiene (hereinafter generally referred to as simply "butadiene") is separated from the remaining $C_4$ hydrocarbons. The remaining $C_4$ hydrocarbons are withdrawn from the butadiene recovery facility primarily as a mixture known in the art as "butene raffinate." This mixture is generally comprised of normal butenes and isobutene. The butadiene recovery facility is generally contiguous to the ethylene production facility for integrated operation.

The recovered butadiene is an important monomer used in the production of a number of polymerization products such as synthetic rubber. It is therefore a material of significant commercial value. Butene raffinate, however, is not a desired by-product of ethylene production and is far less valuable than butadiene or ethylene. Therefore the butene raffinate is, for the most part, used as alkylation plant feed or as fuel. In view of the value of ethylene, particularly when compared to fuel gas, (the current price of ethylene is more than twice that of fuel) the inherent production of butene raffinate during ethylene production seriously detracts from the overall economics of the ethylene process.

Recycling the butene raffinate as a feedstock for the production of ethylene is not desirable due, in part, to the very low yield of ethylene that is produced by the thermal cracking of the raffinate. Indeed, this is true even if the raffinate were hydrogenated prior to cracking because of the high proportion (from 48% to 55%) of isobutane that would be present. The ultimate yield of ethylene resulting from the thermal cracking of isobutane is only about 18%. On the other hand, the isomer of isobutane, i.e., normal butane, is an excellent feedstock for the production of ethylene. Under appropriate cracking conditions, normal butane produces an ultimate yield of about 48% ethylene, which makes it an even better feedstock for the production of ethylene than gas oil or naphtha.

It would be highly desirable therefore to provide a method of converting the butene raffinate generated during ethylene production into normal butane which could be recovered or directed back to the ethylene production process, which method would be efficient, economical and readily integrated into the overall ethylene production process.

Accordingly, it is an object of the present invention to provide a process for converting a stream of unsaturated $C_4$ hydrocarbons, which can include butadiene, into normal butane.

Another object of the invention is to provide a process for converting butene raffinate generated during the production of ethylene into normal butane which can either be recovered, or advantageously, used as one of the feedstocks for the production of ethylene to increase the overall ethylene yield of the ethylene production process.

Still another object of the invention is to provide a process for converting butene raffinate into normal butane feedstock for the production of ethylene, which process can be readily integrated into an ethylene production facility in an efficient and economical manner to increase the overall yield of ethylene.

SUMMARY OF THE INVENTION

In accordance with the present invention there is provided a process for converting unsaturated $C_4$ hydrocarbons into normal butane. The process comprises passing a stream of unsaturated $C_4$ hydrocarbons in contact with hydrogen through a hydrogenation zone to react the hydrogen and the unsaturated $C_4$ hydrocarbons to form normal butane and isobutane. The normal butane and isobutane are discharged from the hydrogenation zone and are introduced into a separation zone to separate the normal butane from the isobutane. The normal butane is discharged and recovered from the separation zone. The isobutane from the separation zone is passed into an isomerization zone to convert a portion of the isobutane into normal butane to form a stream of normal butane and isobutane. Thereafter, the normal butane and isobutane stream formed in the isomerization zone is withdrawn from the isomerization zone. This stream can thereafter be directed to the same separation zone which separates the normal butane and isobutane introduced from the hydrogenation zone to recover additional amounts of normal butane.

In a more specific aspect, the above process is utilized to convert the butene raffinate discharged from a butadiene recovery unit into normal butane. The normal butane is thereafter used as a premium feedstock in an ethylene production process to increase the overall yield of ethylene.

DESCRIPTION OF THE DRAWINGS

FIG. 1 is a block diagram which generally illustrates the treatment zones for converting unsaturated $C_4$ hydrocarbons into normal butane.

FIG. 2 is the preferred arrangement of the apparatus utilized in the treatment zones of FIG. 1. In this arrangement a liquid catalyst is employed in the hydrogenation zone.

FIG. 4 is a schematic diagram illustrating the sequence of treatment zones for the conventional production of ethylene and further showing the utilization of the process for converting butene raffinate, optionally containing butadiene, into normal butane feedstock in conjunction with the conventional process for making ethylene.

FIG. 5 is a fragmentary view of the process of FIG. 4 showing an alternate embodiment of the invention wherein all or a portion of the unsaturated $C_4$ hydrocarbons from the recovery zone are directly introduced into the hydrogenation zone.

Figure 3:
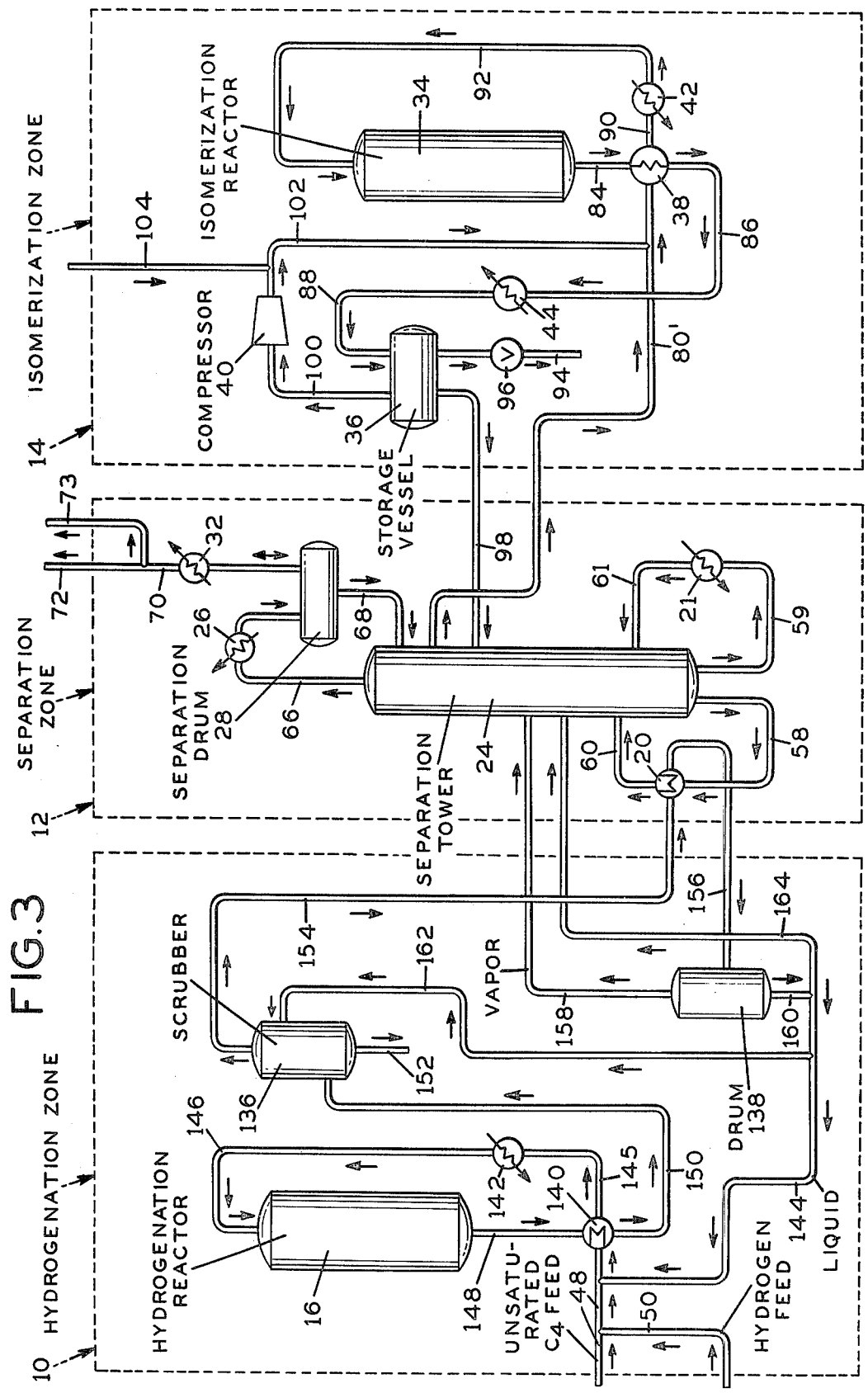
FIG. 3 is another arrangement of the apparatus utilized in the treatment zones of FIG. 1. According to this arrangement a solid catalyst is utilized in the hydrogenation zone.

In these figures, conventional apparatus such as cracked gas compressors, motors, pumps, etc., have generally been omitted so as to more particularly point out and describe the process of the invention.

DETAILED DESCRIPTION OF THE INVENTION

As shown in FIG. 1, the sequence of treatment steps (shown as zones) for converting unsaturated $C_4$ hydrocarbons into normal butane in accordance with the process of the invention, includes: a hydrogenation zone represented by reference numeral 10, a separation zone 12, and an isomerization zone represented by numeral 14.

The preferred arrangement of apparatus utilized in each of the zones of FIG. 1 as well as the pertinent flow characteristics for this arrangement is illustrated in FIG. 2. Thus, referring specifically to FIGS. 1 and 2, it will be seen that the hydrogenation zone 10 includes a hydrogenation reactor 16, a cooler 18, a preheater 22, and a catalyst storage tank 23. The separation zone 12 includes a separation tower 24, a first reboiler 20, a second reboiler 21, an overhead condenser 26, a separation drum 28, and a chiller 32. The isomerization zone 14 includes an isomerization reactor 34, a storage vessel 36, a feed/effluent heat exchanger 38, a compressor 40, and heat exchangers 42 and 44. Other apparatus which may be employed in the process include equipment for the removal of sulfur and water from various process streams. Thus, depending upon the particular catalysts which are employed in hydrogenation zone 10 and isomerization zone 14, it may be necessary to remove sulfur from the unsaturated $C_4$ hydrocarbon feed stream or from other internal streams; this can be done by using conventional equipment for the removal of sulfur such as a caustic washing unit (not shown). Also, it may be desirable to remove water from the unsaturated $C_4$ hydrocarbon feed or from other streams such as from separation tower overhead line 66, isobutane stream line 82, etc.; this can be effected by means of conventional equipment for the removal of water such as a distillation tower or an adsorption tower (not shown) or by adjusting the conditions in separation tower 24. Generally, the necessity for removing water from the process streams will depend on the type of catalysts employed in hydrogenation zone 10 and isomerization zone 14 and the degree to which it is desired to cool the purge gases in separation zone 12.

In the first stage of the process, a feed of unsaturated $C_4$ hydrocarbons is hydrogenated in hydrogenation zone 10 to form a stream of normal butane and isobutane. Thus, with specific reference to FIG. 2, a hydrocarbon feed comprised of unsaturated $C_4$ hydrocarbons is initially directed through line 48 into a hydrogenation reactor 16 in hydrogenation zone 10. In hydrogenation reactor 16, the unsaturated $C_4$ hydrocarbons are reacted with hydrogen, which is introduced into reactor 16 through line 50, to form normal butane and isobutane. The reaction is conducted in the presence of a catalyst and in the process of FIG. 2 a liquid catalyst is used. Hydrogenation reactor 16 can be any reactor suitable for effecting a hydrogenation reaction. It is preferred that hydrogenation reactor 16 be a vessel without internals suitable for use with a soluble catalyst.

The unsaturated $C_4$ hydrocarbon feed introduced into hydrogenation reactor 16 can contain some or all of the $C_4$ hydrocarbons, i.e., butene-1, cis-butene-2, trans-butene-2, isobutene, 1,3-butadiene plus quantities of vinyl acetylene, ethyl acetylene, 1,2-butadiene, normal butane, isobutane, $C_3$ hydrocarbons, $C_5$ hydrocarbons and the like. This feed can be obtained from a number of sources such as from a petroleum refinery or a petrochemical facility. Preferably the feed is a mixture comprised of normal butenes and isobutene known as "butene raffinate" which is discharged from a butadiene recovery unit. As an alternative to the butene raffinate feed, the unsaturated $C_4$ hydrocarbon feed can be the butadiene rich $C_4$ hydrocarbon by-product from an ethylene production facility. When this feed is used more hgydrogen is required than when butene raffinate is used and more external cooling is needed to remove the increased exothermic reaction heat.

The hydrogen introduced into hydrogenation reactor 16 can also be obtained from a variety of sources, so long as it is of high purity and relatively free of hydrogenation catalyst poisons such as acid gases and heavy metals. Because of its ready availability, particularly when butene raffinate is the $C_4$ hydrocarbon feed, the hydrogen generated in the demethanization zone of an ethylene production facility, which is normally available at from 90 to 95% purity, is an excellent source of hydrogen for introduction into hydrogenation reactor 16. Advantageously, therefore, all of the raw materials utilized for the production of normal butane in accordance with the process are readily available at an ethylene production facility. Moreover, since the normal butane product of the process can be recycled as one of the feedstocks to the ethylene production facility to increase the overall yield of ethylene, the present invention provides an economical and efficient method for increasing the production of ethylene at an ethylene production facility.

Referring now to the hydrogenation reaction which occurs in hydrogenation reactor 16, as is known, the hydrogenation of unsaturated $C_4$ hydrocarbons is usually conducted in the presence of a catalyst in order to speed the rate of reaction, which would otherwise be unduly slow, even at elevated temperatures. Hydrogenation reactions are usually conducted in the presence of conventional catalysts such as nickel, platinum or palladium. Depending on the catalysts used, different temperatures and pressures are employed to carry out the hydrogenation reaction. Some typical catalysts operate with hydrocarbons in the vapor phase at temperatures of about 100°–250° F. and pressures of about 100–200 psig. According to the process of the present invention, a hydrogenation catalyst is employed which permits operations in hydrogenation reactor 16 at temperature levels particularly suited for heating selected streams in the process so that the amount of external heating needed for conducting the overall process of the invention is minimized. The catalysts that can be employed in the present invention are those which permit operations in hydrogenation reactor 16 at temperatures of about 200° F. to about 450° F., and preferably about 250° F., and pressures of from about 100 to about 500 psig and preferably at about 400 psig. At these temperatures the heat generated in hydrogenation reactor 16 can be utilized, for example, as the source of heat for preheating the feed to isomerization reactor 34 and for reboiling the liquid in first reboiler 20.

A wide variety of hydrogenation catalysts which are adapted to operate within the above described selected conditions can be employed in the process of the invention. Among the catalysts which can be used are the conventional heterogeneous phase catalysts and the conventional liquid phase catalysts. The preferred hydrogenation catalysts are the conventional liquid phase catalysts. FIG. 2 illustrates the process of the invention employing these liquid phase catalysts. Illustrative of the liquid phase catalysts suitable for use in the process are the soluble homogeneous hydrogenation catalysts disclosed in U.S. Pat. Nos. 3,655,799; 3,663,635 and 3,784,481 and in the publication, Hydrocarbon Processing, *Maximize Ethylene By Hydrogenation,* Vol. 56, No. 1, January 1977, page 131, which disclosures are incorporated herein by reference. The most preferred catalyst for use in the hydrogenation reaction is the commercially available homogeneous liquid phase catalyst known as Vapidrol, which is available from the company, Institut Francais du Petrole, located in Rueil-Malmaison, France. This catalyst permits operation in the hydrogenation reactor at the preferred temperature of about 250° F. at the top of the reactor and the preferred pressure of about 400 psig.

While the catalysts employed for the hydrogenation reaction are preferably of the liquid phase type, heterogeneous phase catalysts can also be employed as indicated above. Among the heterogeneous phase catalysts which can be used in the Girdler G-55 catalyst disclosed in U.S. Pat. No. 3,098,882, which disclosure is also incorporated herein by reference. It will be clear that when heterogeneous phase catalysts are used, the preferred process of the invention illustrated in FIG. 2 is varied somewhat. FIG. 3 illustrates one such variation of the process to employ the heterogeneous catalyst. The description of the process shown in FIG. 3 will be discussed in detail hereafter.

Referring again to the process shown in FIG. 2, it will be seen that the liquid phase hydrogenation catalyst along with recycled hydrocarbons is fed through line 52 into a circulating reaction mass in hydrogenation reactor 16 wherein the catalyst contacts the unsaturated hydrocarbon feed and the hydrogen gases.

As the unsaturated hydrocarbon feed and hydrogen gases contact the liquid catalyst in reactor 16, they react with the evolution of sufficient heat to convert the unsaturated hydrocarbons to a gaseous mixture of normal butane and isobutane which leaves the top of reactor 16 through line 51. These gases are thereafter directed to the separation zone 12 or, the gases may be subjected to further hydrogenation in a separate hydrogenation reactor (not shown) before passage to separation zone 12.

As indicated above, the liquid reaction mass in reactor 16, which is heated by the heat released during the hydrogenation reaction, can advantageously be used as a source of heat for first reboiler 20 of separation tower 24 and as the heating fluid for preheater 22 of isomerization reactor 34. Thus, the heated reaction mass, principally comprised of liquid catalyst and normal butane and isobutane, exits hydrogenation reactor 16 through line 54 and is directed into preheater 22 where it is passed in indirect contact with a stream rich in isobutane which is discharged from separation tower 24.

The reaction mass exiting preheater 22 is still hot enough to reboil the bottoms of separation tower 24. Hence, the liquid reaction mass discharged from preheater 22 through line 56 is passed through first reboiler 20 in indirect contact with the bottoms liquid of separation tower 24 to reboil the bottoms liquid which is directed into the reboiler through line 58. Reboiler 20 can be a conventional shell and tube heat exchanger.

It is preferred that the reaction mass discharged from first reboiler 20 be subjected to further cooling prior to returning it to hydrogenation reactor 16. Thus, the reaction mass exiting first reboiler 20 through line 62 is introduced into cooler 18 wherein it is cooled to a temperature of about 250° F. The cooled liquid reaction mass is discharged from cooler 18 through line 52 and is re-introduced into the upper portion of hydrogenation reactor 16 for further contacting with the hydrogenation reactants.

As will be seen in FIG. 2, liquid catalyst is continuously added to the system from catalyst storage tank 23 through line 64. During operation of the process the liquid catalyst becomes spent. The spent catalyst is intermittently removed to provide greater efficiency.

Referring again to the stream comprised of normal butane and isobutane produced in hydrogenation reactor 16 which exits the reactor through line 51, it is desired to separate this stream into its two principal components so that the normal butane can be recovered as a product of the process and the isobutane can be isomerized to provide additional quantities of normal butane. Accordingly, referring again to FIGS. 1 and 2, the normal butane-isobutane stream discharged from hydrogenation reactor 16 is directed through line 51 into separation tower 24 situated in separation zone 12. Separation tower 24 can be any apparatus suitable for separating normal butane from isobutane. Preferably, separation tower 24 is a conventional multistage distillation tower wherein the temperatures, pressures and flows are controlled and a plurality of trays or conventional packed sections are provided to separate normal butane from isobutane. The operating temperatures and pressures of separation tower 24 can range from about 100° F. to about 200° F. and about 55 to about 240 psig at the top of the tower, and from about 133° to about 235° F. and about 65 to about 250 psig at the bottom of the tower. Separation tower 24 can be operated at an overhead temperature as low as about 50° F., although such low temperatures are generally undesirable.

The principal component of the overhead vapors from separation tower 24 is isobutane which exits tower 24 through line 66 and is introduced into overhead condenser 26 wherein all or a portion of the vapors are condensed. The mixture exiting from overhead condenser 26 flows to separation drum 28 from which liquid flows as reflux to separation tower 24 and uncondensed vapors pass through line 70 into chiller 32. In chiller 32 some liquid is condensed and is returned to separation drum 28. The uncondensed vapors, comprising principally methane, unreacted hydrogen and uncondensed isobutane, are withdrawn from the system through lines 72 or 73. Advantageously, these uncondensed vapors are directed through line 72 to the quench prefractionation and compression zone 110 of an ethylene production facility to recover additional amounts of by-product.

Part of the reboiler heat for separation tower 24 is supplied by the liquid reaction mass leaving hydrogenation reactor 16 after the liquid reaction mass has first been passed through preheater 22. Thus, a liquid comprising principally normal butane is withdrawn as a stream from separation tower 24 through line 58 at a temperature of about 133° F. to about 235° F., corresponding to tower pressures of about 65 psig to 250 psig, respectively, and is introduced into first reboiler 20. The heated normal butane leaves first reboiler 20 through line 60 in a partially vaporized state and is directed back to separation tower 24 where the vapor portion of the reboiler effluent provides stripping vapor for the separation tower 24. The balance of the reboiler heat required for separation tower 24 is supplied by using second reboiler 21 which is generally heated by condensing steam and is of a conventional type. Reboiler 21 receives liquid from the base of separation tower 24 through line 59 which is returned as a mixture of vapor and liquid to tower 24 through line 61.

The bottoms liquid of separation tower 24 is principally comprised of normal butane which is a primary product of the process of the invention and is withdrawn as a liquid from tower 24 through line 74. This normal butane stream can be recovered for shipment to outside uses or, alternatively, it can be introduced into a cracking furnace (not shown) of an ethylene production facility (as seen in FIG. 4) to provide an excellent feedstock for the production of ethylene. The normal butane product can be supplied at about 95 mol% normal butane.

The isobutane rich stream separated in separation tower 24 is discharged as a liquid from tower 24 through line 80. It is preferred to convert the isobutane in this stream into normal butane. This can be effected by passing the isobutane rich stream into contact with an isomerization catalyst in isomerization reactor 34 under reaction conditions suitable for the production of normal butane. The effluent stream from the isomerization reactor can then be recycled to separation tower 24 to recover additional amounts of normal butane and to recycle the unconverted isobutane for further isomerization treatment. The process is preferably operated to isomerize the isobutane to extinction to provide a maximum amount of normal butane. Alternatively, a partial re-cycling of isomerized product can be employed to provide two product streams; one comprised of normal butane and the other comprised of both normal butane and isobutane or, part of isobutane stream 80 can be withdrawn as an isobutane product.

Thus, as will be seen in FIGS. 1 and 2, the isobutane rich stream from separation tower 24, which is at a temperature of from about 110° F. to about 220° F. and a pressure of from about 55 psig to about 240 psig, is directed to preheater 22 through line 80 and thereafter to isomerization zone 14 through line 82. The heated isobutane stream is withdrawn from the preheater through line 82 at a temperature of about 160° F. to about 230° F. and is directed into feed effluent heat exchanger 38 wherein it is subjected to additional heating by indirect contact with the effluent from isomerization reactor 34.

It is desired to subject the isobutane rich stream discharged from feed effluent heat exchanger 38 to additional heating in heat exchanger 42. The isobutane rich stream is thus introduced into heat exchanger 42 through line 90. Heat exchanger 42 can comprise one or more conventional stream heated exchangers or, if high isomerization temperatures, so require, the steam heated exchangers can be replaced or supplemented by one or more high temperature heaters such as conventional direct fired heaters (not shown). The isobutane is withdrawn from heat exchanger 42 through line 92 at a temperature of about 250° F. to about 950° F. and a pressure of about 250 psig to about 700 psig.

The isobutane rich stream discharged from heat exchanger 42 is at the desired temperature and pressure for introduction into isomerization reactor 34 and, thus, this stream is introduced into isomerization reactor 34 through line 92 wherein the isobutane is directed into intimate contact with an isomerization catalyst to convert a portion of the isobutane into normal butane. Isomerization reactor 34 can be any conventional reactor suitable for contacting a hydrocarbon feed with an isomerization catalyst.

The isomerization catalyst employed in isomerization reactor 34 is conventional and is used to effect the isomerization of isobutane into normal butane. A wide variety of conventional catalysts can be employed for this purpose. Among these catalysts are the conventional platinum or palladium (0.01-1.0 wt%) on alumina catalysts activated by a chlorohydrocarbon. Other catalysts which can be employed include bauxite or quartz chips impregnated with aluminum chloride or aluminum bromide. Other catalysts that can be used are the noble or non-noble metal catalysts incorporated on a base carrier or support. Conventional liquid phase catalysts containing, e.g., $ALCL_3$ can also be used. Further information about many of the aforementioned catalysts, as well as other catalysts suitable for use in the isomerization reaction of the invention, including details about process procedures and conditions utilizing these catalysts, is contained in the publication, *Proceedings Seventh World Petroleum Congress*, Vol. 4, pp. 135-145 (1967), which disclosure is incorporated herein by reference.

Heretofore, the isomerization catalysts of the type described above have generally been employed to effect exactly the reverse reaction than the one employed herein, i.e., the conversion of normal butane into isobutane. This reverse reaction is frequently employed to furnish isobutane which is used in the preparation of a high octane gasoline component known as alkylate. Alkylate is generally prepared by reacting isobutane with olefins such as propylene or butylene.

As is shown, isobutane-normal butane reactions are equilibrium reactions which favor the production of normal butane under certain conditions and the production of isobutane at other conditions. In accordance with the process of the invention the reaction conditions in reactor 34 are set such that the production of normal butane is favored. In the presence of the above described catalysts favorable conversion of isobutane is obtained in the process of the invention by maintaining the inlet temperature in the isomerization reactor from about 250° to about 95° F., and the inlet pressure from about 250 to about 700 psig. The outlet temperature of the reactor 34 is from about 210° to about 910° F. and the outlet pressure is about 210 to about 660 psig. The space velocity in isomerization reactor 34 can range from about 0.1 to about 10 vol./vol./hr.

Under these conditions the effluent from the isomerization reactor 34 can be from about 34 to 70 mol % isobutane and about 30 to 60 mol % normal butane, with the remainder of the effluent comprising minor portions of hydrogen, methane, ethane, propane, each at about 1 to 3 mol % and $C_5$ hydrocarbons at about 0.1 to 1.5 mol %. Equilibrium conditions are approached at the outlet of isomerization reactor 34. By-product formation in isomerization reactor 34 is reduced by the presence of hydrogen which is introduced through line 104.

It is preferred to cool the effluent from reactor 34. Thus, referring to FIG. 2, the effluent gas stream from isomerization reactor 34 now enriched in normal butane is withdrawn from the reactor through line 84 and is passed in indirect contact with the isobutane rich feed in feed effluent heat exchanger 38. The effluent is thereafter directed through line 86 to heat exchanger 44 which cools the stream by indirect contact with cooling water to a temperature of about 100° F. At this temperature most of the normal butane and isobutane are condensed and little of them remain in the noncondensed portion of this stream. The cooled effluent stream, enriched in normal butane is thereafter directed through line 88 into storage vessel 36 wherein a stream comprised of normal butane and isobutane can be recovered through line 94 as another product stream of the process by opening valve 96.

Preferably, however, all of the liquid contents of vessel 36 are recycled to separation tower 24 to recover greater amounts of normal butane from separation tower 24. This recycling can be effected by closing valve 96 and directing the liquid contents of vessel 36 back to separation tower 24 and directing the vapor portion in vessel 36 back to isomerization reactor 34. Thus, referring again to FIGS. 1 and 2, a stream of normal and isobutane containing small amounts of hydrogen and methane which is at a temperature of about 100° F. and a pressure of about 190 to about 630 psig is directed from vessel 36 back into separation tower 24 through line 98 for further distillation treatment.

The vapor in vessel 36 is withdrawn through line 100 and is directed back to isomerization reactor 34. This vapor, rich in hydrogen and containing a small amount of methane, is used to stabilize the isomerization reaction. Prior to returning the gas to isomerization reactor 34, it is desired to increase the pressure of this stream and to add hydrogen to the vapor. Thus, referring to FIG. 2, the vapors withdrawn from vessel 36 are initially directed through line 100 into compressor 40 wherein the pressure of the stream is increased to about 270 psig to about 740 psig. The compressed gas stream is discharged from compressor 40 through line 102 and is combined with hydrogen which is introduced into line 102 through line 104. The added hydrogen can be provided from the demethanization zone of an ethylene production facility. The combined stream in line 102 is thereafter introduced into line 82 where it merges with the isobutane rich stream discharged from preheater 22. The merged stream in line 82 is thereafter directed into heat exchangers 38 and 42 for further heating prior to introduction of the combined feed into isomerization reactor 34. Optionally a hydrogenation step using a hydrogenation reactor (not shown) can be inserted in line 90 or line 92 if the proportion of unsaturated hydrocarbons entering isomerization reactor 34 should otherwise be too high.

Figure 6:
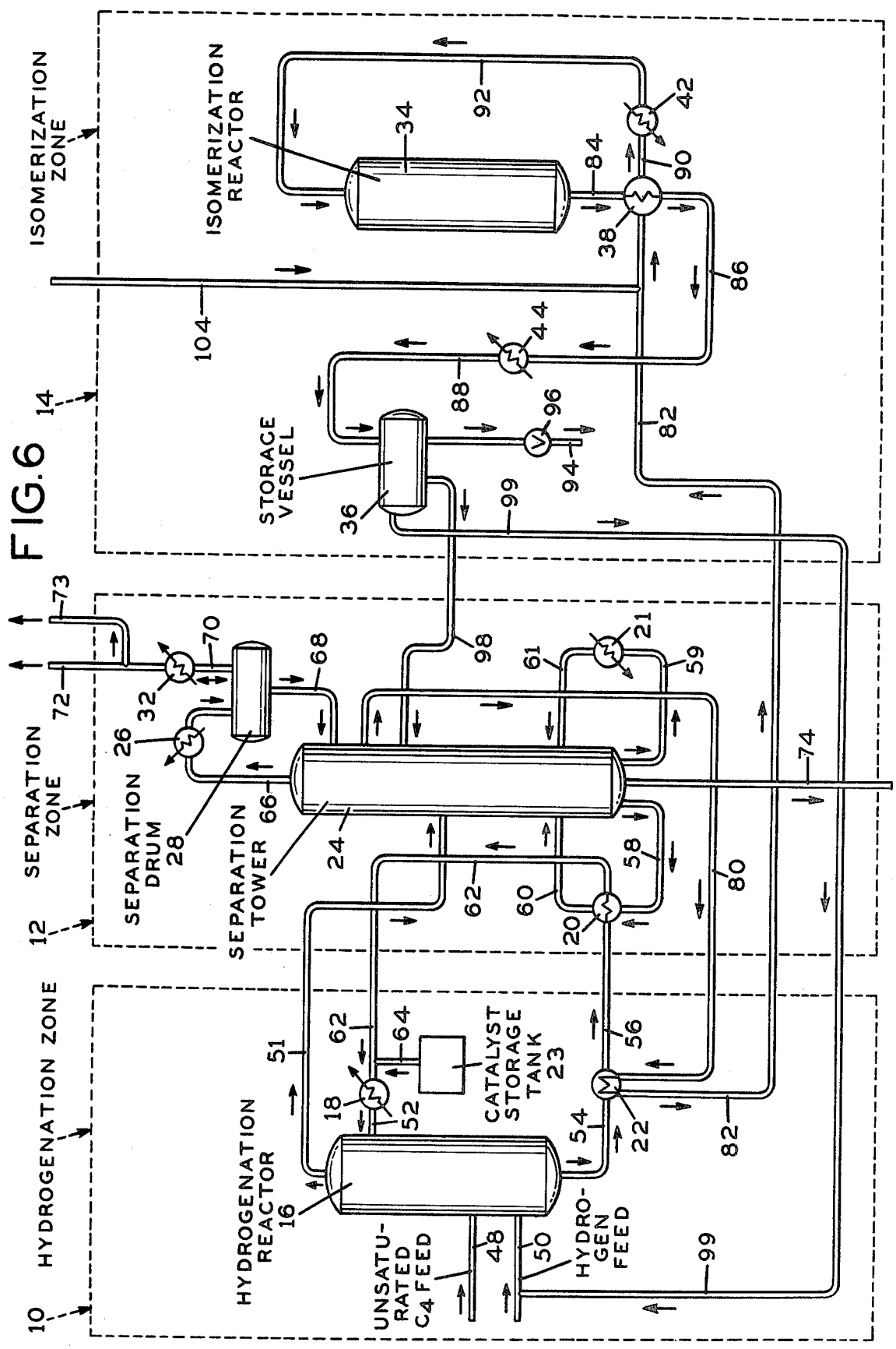
FIG. 6 is an arrangement of the apparatus similar to FIG. 2 showing an alternate use for the gases in storage vessel 36.

An another alternative, rather than directing hydrogen and methane gases back to isomerization reactor 34, these gases can be utilized in hydrogenation zone 10 as a part of the feed for hydrogenation reactor 16. Thus, as will be seen in FIG. 6, according to this alternative compressor 40, utilized to recycle the gases to isomerization reactor 34, is eliminated and the gases in storage vessel 36 are directed through line 99 into hydrogenation reactor 16 through line 50. When it is desired to utilize the gases in storage vessel 36 in this manner, a compressor (not shown) can be employed in line 104 or in line 99 if the relative pressures in hydrogenation reactor 16 and isomerization reactor 34 so require.

The process of the invention for converting unsaturated $C_4$ hydrocarbons into normal butane has been described in detail hereinabove with particular reference to the preferred system shown in FIG. 2. This system utilizes a liquid phase catalyst in hydrogenation zone 10. As indicated above, heterogeneous phase hydrogenation catalysts can also be used for the hydrogenation reaction. When a heterogeneous phase catalyst is used certain variations in the process illustrated in FIG. 2 are employed. FIG. 3 illustrates a process for converting unsaturated $C_4$ hydrocarbons into normal butane which uses heterogeneous phase hydrogenation catalysts in hydrogenation zone 10. It will be seen that the process depicted in FIG. 3 is essentially the same as the process of FIG. 2. (To the extent possible, like parts of FIGS. 1 and 2 are represented by like numerals in FIG. 3). Thus, the process of FIG. 3 also includes a hydrogenation zone 10, a separation zone 12 and an isomerization zone 14. The product stream and feed streams in FIG. 3 are the same as in FIG. 2, e.g., the unsaturated $C_4$ hydrocarbons are introduced through line 48, hydrogen is introduced through line 50 and normal butane is recovered through line 74. Operation in separation zone 12 of FIG. 3 is also substantially the same as in FIG. 2. Thus, the saturated hydrocarbon feed produced in hydrogenation zone 10 is introduced into separation tower 24 wherein the normal butane product is separated and recovered through line 74 and the isobutane rich stream is withdrawn through line 80' for further treatment in the isomerization zone. It will be seen that the treatment steps for the overhead and bottoms streams of separation tower 24 in FIG. 3 are substantially the same as in FIG. 2. Thus, the overhead vapors from tower 24 are partially condensed in condenser 26 and the vapors are vented from the system through lines 72 or 73. The liquid resulting from the condensation is returned to tower 24 as a reflux through line 68. The process steps in isomerization zone 14 of FIG. 3 are also essentially the same. The isobutane rich stream discharged from separation tower 24 through line 80' is introduced into isomerization reactor 34 through line 92 after it has been preheated in heat exchangers 38 and 42 (according to this embodiment the isobutane stream is not preheated in preheater 22). The effluent from isomerization reactor 34 is directed through heat exchanger 38 to preheat the isomerization reactor feed and is then introduced into storage vessel 36. As in FIG. 2, the liquid contents of vessel 36 are recycled to separation tower 24 to recover additional normal butane product and the vapors in vessel 36 are returned to isomerization reactor 34 after they have been compressed and admixed with a small amount of make-up hydrogen which is introduced through line 104.

Referring now to hydrogenation zone 10 shown in FIG. 3, it will be seen that this zone includes a hydrogenation reactor 16, a scrubber 136, a drum 138 and heat exchangers 140 and 142. As will be seen in FIG. 3 the unsaturated $C_4$ hydrocarbon feed introduced through line 48 is combined with hydrogen which is introduced into line 48 through line 50. The combined feed is merged with liquid reactor effluent which is introduced into line 48 through line 144. The merged feed in line 48 is passed through heat exchanger 140 and thereafter through line 145 into heat exchanger 142 before it is introduced as a vapor into hydrogenation reactor 16 through line 146. Hydrogenation reactor 16 of FIG. 3 can be any reactor suitable for effecting contact between the feed stream and a heterogeneous catalyst such as the Girdler G-55 catalyst identified above. Preferably hydrogenation reactor 16 is a conventional fixed bed reactor. The effluent from hydrogenation reactor 16, which is principally comprised of a mixture of normal butane and isobutane, can contain certain amounts of high molecular weight compounds, such as polymerization products, which are usually formed when heterogeneous hydrogenation catalysts are employed in, e.g., fixed bed reactors. It is desired to remove these high molecular weight compounds from the reactor effluent stream prior to introducing this stream into separation tower 24. Thus, the effluent from reactor 16 is withdrawn from reactor 16 through line 148 and is passed through heat exchanger 140 and then introduced through line 150 into scrubber 136. Scrubber 136 can be a conventional packed tower or plate tower. The high molecular weight compounds separated from the normal butane-isobutane stream are removed from scrubber 136 through line 152. The mixture of normal butane and isobutane in scrubber 136 is withdrawn from scrubber 136 through line 154 and is passed in heat exchange contact with a bottoms stream from separation tower 24 in first reboiler 20 to reboil the bottoms liquid. The normal butane-isobutane stream is discharged from first reboiler 20 through line 156 and is introduced into drum 138. A vaporous mixture of normal butane and isobutane is withdrawn from drum 138 through line 158 and is introduced into separation tower 24 to separate the normal butane from the isobutane. The liquid in drum 138 is withdrawn from the drum through line 160. A portion of this liquid stream, which is principally comprised of a mixture of butane and isobutane, is returned through line 144 to the reactor feed in line 48. Another portion of this liquid is diverted from line 144 through line 162 into scrubber 136 as a convenient scrubbing agent for the scrubbing unit. The remaining portion of the liquid from drum 138 is introduced into separation tower 24 through line 164.

Heat exchange conditions in FIG. 3 differ from those of FIG. 2.

As will be discerned from the foregoing, a process has been provided which is particularly suited for the conversion of unsaturated $C_4$ hydrocarbons into normal butane. It will be clear that variations in this process can be accomplished which presently are, however, not as desirable because, e.g., unwanted cracking or other side reactions may occur. Process variations may also require difficult separation operations, necessitating burdensome tasks such as the separation of butene-1 from isobutene.

As illustrative, in one such variation of the process, an unsaturated $C_4$ hydrocarbon stream containing normal butenes and isobutene is first introduced into isomerization zone 14 wherein the isobutene is isomerized into normal butenes. The isomerized butenes stream is withdrawn from the isomerization zone 14, and is thereafter introduced into separation zone 12 wherein a normal butenes stream is produced and separated from isobutene. The normal butenes stream produced in the separation zone is then introduced into hydrogenation zone 10 wherein it is converted into normal butane. According to this variation of the process the isobutene rich stream generated in the separation zone can, if desired, by recycled to the isomerization zone for further isomerization treatment.

In still another variation of the process, a stream of unsaturated $C_4$ hydrocarbons containing normal butenes and isobutene is introduced into the separation zone wherein a normal butenes stream is separated from an isobutene stream. The separated normal butenes stream is thereafter converted into normal butane in the hydrogenation zone and recovered. The isobutene stream separated in the separation zone is thereafter directed into the isomerization zone wherein it is isomerized so that a stream containing normal butenes and isobutene is produced and thereafter recycled to the separation zone to produce further amounts of the normal butenes stream. The butene stream is thereafter hydrogenated in the hydrogenation zone into a normal butane product.

In still another process variation, an unsaturated $C_4$ hydrocarbon stream containing normal butenes and isobutene is introduced into separation zone 12 wherein a normal butenes stream is separated from a stream enriched in isobutene. The separated normal butenes stream is hydrogenated to normal butane product in the hydrogenation zone and the isobutene enriched stream separated in the separation zone is directed to a separate hydrogenation zone. The output of the hydrogenation zone is thereafter directed to the isomerization to form a stream comprised of normal butane and isobutane which is thereafter directed through a separation zone for recovery of additional amounts of normal butane. The isobutane rich stream which is produced in the separation zone can be recycled to the isomerization zone to produce further amounts of normal butane. Alternatively, if the normal butenes content of the isobutene stream is high enough to warrant it, the hydrogenated isobutene cut can be passed to a separation zone wherein normal butane is withdrawn as an added product and isobutane is recycled to the isomerization zone.

As indicated above, the process of the present invention, and especially the process illustrated in FIG. 2, is particularly suited for operation in conjunction with an ethylene production process to increase the yield of ethylene produced by the process. Thus, referring specifically to FIG. 4, wherein the process for converting unsaturated $C_4$ hydrocarbons is shown in conjunction with a conventional process for making ethylene and wherein like parts of FIGS. 1, 2 and 3 to the extent possible, are represented by like numerals in FIG. 4, the sequence of conventional treatment steps for producing ethylene includes a cracking zone 106, a rapid cooling zone 108, a quench prefractionation and compression zone 110, a demethanization zone 112, a recovery zone 114 and a butadiene recovery zone 116 (which may be contiguous to the ethylene production facility).

The hydrocarbon feed for the conventional ethylene process, which can include gas oil or naphtha or mixtures thereof is initially introduced into cracking zone 106 through line 118 wherein the feed is converted in cracking furnaces (not shown) into ethylene and a variety of co-products and by-products such as hydrogen, methane, propylene, $C_4$ unsaturated hydrocarbons and pyrolysis gasoline. The cracked gas stream is discharged from cracking zone 106 through line 120 and is introduced into rapid cooling zone 108. The cooled gas is thereafter introduced through line 122 into a quench prefractionation and compression zone 110 wherein a heavy oil fraction is removed and the gases are compressed to the desired pressure levels for separation in demethanization zone 112 and recovery zone 114.

The compressed gases are thereafter introduced through line 124 into demethanization zone 112 wherein methane is removed and a stream of hydrogen is generated. A portion of the hydrogen produced in the demethanization zone 112 is directed through line 50 into hydrogenation zone 10 for introduction into hydrogenation reactor 16. Another portion of the hydrogen produced in demethanization zone 112 is directed into isomerization zone 14 through line 104 into line 102 where it is admixed with the vapor stream comprising primarily hydrogen, normal butane and isobutane which is recycled to isomerization reactor 34 (FIGS. 2 and 3). The demethanized gases from demethanization zone 112 are thereafter directed through line 126 into recovery zone 114 wherein ethylene, propylene, unsaturated $C_4$ hydrocarbons and pyrolysis gasoline products are separated and/or recovered by means of a series of fractional distillation towers (not shown).

The unsaturated $C_4$ hydrocarbon stream separated in the recovery zone 114 is directed through line 128 into butadiene recovery zone 116 wherein butadiene is separated and recovered through line 130. Except for several minor vent and residue streams, the remainder of the unsaturated $C_4$ hydrocarbons in butadiene recovery zone 116 comprises the butene raffinate stream. The butene raffinate is discharged from butadiene recovery zone 116 and is introduced into hydrogenation zone 10 through line 48. The butiene raffinate is thereafter treated in accordance with the process steps of the invention as described previously to produce the normal butane product. The normal butane product is discharged from separation zone 12 through line 74 and is introduced into cracking zone 106 as an excellent feedstock for the production of ethylene. As indicated previously, the vapors vented from separation zone 12 are recycled to the quench prefractionation and compression zone 110 through line 72 to recover additional by-products.

FIG. 5 shows an alternate embodiment of the process of the invention for producing ethylene wherein some or all of the $C_4$ unsaturated hydrocarbons generated in recovery zone 114 bypass treatment in the butadiene recovery zone 116 entirely. According to this embodiment, some or all of the unsaturated $C_4$ hydrocarbons separated in recovery zone 114 are directly introduced through line 131 into hydrogenation zone 10 for hydrogenation treatment.

In accordance with the process of the invention, unsaturated $C_4$ hydrocarbons from outside sources can be employed to provide additional amounts of normal butane feedstock for the production of ethylene. For example, as seen in FIG. 4, a stream of unsaturated $C_4$ hydrocarbons, which could be obtained from catalytic cracking or other thermal cracking processes, can be introduced into the process sequence through line 132 to supply additional normal butane feedstock. As another alternative, a stream of normal and isobutane supplied from, for example, natural gas condensate, could be introduced through lines 134 or 135, depending on the ratio of normal butane to isobutane, to further increase the amount of normal butane feedstock.

The following Tables I and II demonstrate the increase in ethylene yield using the process of the invention. Table I is an overall material balance for an ethylene production process which utilizes the process of the invention for converting butene raffinate into normal butane feedstock illustrated in FIG. 2. The information in Table I is for an ethylene production process wherein 650,000 metric tons of ethylene per year (1.43 billion lbs./yr.) of 99.92 mol % purity are produced in 8160 operating hours per year from a naphtha and gas oil feedstock. Table II indicates a material balance for the same process for producing ethylene in the same amounts and purity except that the process for which Table II is a material balance does not employ the process of the invention for converting butene raffinate into normal butane feedstock.

From a comparison of the material balances in Tables I and II it will be seen that for the same ethylene output, the quantity of naphtha and gas oil feedstock required is 7.3% less when the process of the invention for converting butene raffinate into normal butane feedstock is employed. The ethylene yield has increased from 26.78 weight % for the prior art process (Table II) to 28.90 weight % for the process for making ethylene in accordance with the invention (Table I). Advantageously, the propylene yield has also risen from 12.9 weight % to 13.7 weight %.

Table III shows the specific process flow characteristics, including temperatures, pressures and flow rates, for the part of the process of Table I which converts the butene raffinate into normal butane feedstock in accordance with the flow diagram of FIG. 2.

TABLE I

OVERALL MATERIAL BALANCE FOR THE PRODUCTION OF
ETHYLENE UTILIZING THE PROCESS OF THE INVENTION

Heavy Naphtha and Gas Oil Feed

TABLE I-continued

| (4.967 billion lb/yr) | | Product Distribution (lb/hr) | | | | | | |
|---|---|---|---|---|---|---|---|---|
| I. Heavy Naphtha Feed (2.739 billion lb/yr) Properties: | | Hydrogen Product | Fuel Gas | Ethylene Product | $C_3H_6$ Product | $C_4{}^s$ Product | Gasoline Product | Fuel Oil |
| | Hydrogen | 3016 | 618 | — | — | — | — | — |
| Specific Gravity 0.773 | Methane | 1263 | 77949 | 30 | — | — | — | — |
| Initial Boiling Point 240° F. | Ethylene | — | 301 | 175612 | — | — | — | — |
| (ASTM Distillation) | Ethane | — | — | 94 | 24 | — | — | — |
| Final Boiling Point 385° F. | Propylene | — | — | — | 83428 | — | — | — |
| (ASTM Distillation) | Propane | — | — | — | 45 | — | — | — |
| | 1,3-Butadiene | — | — | — | — | 31811 | 357 | — |
| Composition of Heavy Naphtha (wt %) | Other $C_4{}^s$ | — | — | — | — | — | 558 | — |
| | $C_5{}^s$ | — | — | — | — | — | 25682 | — |
| Paraffins 21.8 | Benzene | — | — | — | — | — | 40275 | — |
| Olefins 22.6 | Other $C_6{}^s$ | — | — | — | — | — | 12357 | — |
| Naphthenes 37.5 | Toluene | — | — | — | — | — | 21218 | — |
| Aromatics 18.1 | Other $C_7{}^s$ | — | — | — | — | — | 4270 | — |
| Wt % Sulfur 0.1 | Xylenes | — | — | — | — | — | 9456 | — |
| Wt % $H_2$ 14.19 | Ethyl Benzene | | | | | | | |
| BMCI Index 21.9 | & Styrene | — | — | — | — | — | 11815 | — |
| | Other $C_8{}^s$ | — | — | — | — | — | 1800 | — |
| Steam to Hydrocarbon wt ratio - 0.6 | $C_9$ - 400° F. | — | — | — | — | — | 16611 | — |
| | Fuel Oil | — | — | — | — | — | — | 90056 |
| II. Gas Oil Feed (2.588 billion lb/yr) Properties: | Total | 4278 | 78869 | 175736 | 83497 | 31811 | 144399 | 90056 |
| Specific Gravity 0.854 | | | | | | | | |
| Initial Boiling Point 550° F. (ASTM) | | | | | | | | |
| Final Boiling Point 630° F. (ASTM) | | | | | | | | |

Composition of Gas Oil (wt %)
Wt % Sulfur         %)
Wt % Sulfur         0.2-0.3
Wt. % $H_2$         13.41
BMCI Index          31.90
Steam to Hydrocarbon wt ratio - 0.8

COMPONENT YIELDS BASED ON A SINGLE PASS CONVERSION OF 100 PARTS BY WEIGHT FEED

| | |
|---|---|
| Hydrogen | 0.60 |
| Methane | 13.02 |
| Ethylene | 28.90 |
| Ethane | 0.02 |
| Propylene | 13.70 |
| Propane | 0.01 |
| 1,3-Butadiene | 5.29 |
| Other $C_4{}^s$ | 0.09 |
| $C_5{}^s$ | 4.22 |
| Benzene | 6.62 |
| Other $C_6{}^s$ | 2.03 |
| Toluene | 3.49 |
| Other $C_7{}^s$ | 0.70 |
| Xylenes | 1.55 |
| Ethyl Benzene & Styrene | 1.94 |
| Other $C_8{}^s$ | 0.30 |
| $C_9$ - 400° F. | 2.73 |
| Fuel Oil | 14.79 |
| Total | 100.00 |

TABLE II

OVERALL MATERIAL BALANCE FOR THE SAME PROCESS FOR PRODUCING ETHYLENE AS THE PROCESS OF TABLE I WITHOUT CONVERTING BUTENE RAFFINATE INTO NORMAL BUTANE FEEDSTOCK

| Heavy Naphtha and Gas Oil Feed (5.360 billion lb/yr) | | Product Distribution (lb/hr) | | | | | | |
|---|---|---|---|---|---|---|---|---|
| I. Heavy Naphtha Feed (2.5677 billion lb/yr) Properties: | | Hydrogen Product | Fuel Gas | Ethylene Product | $C_{36}$ Product | $C_4{}^s$ Product | Gasoline Product | Fuel Oil |
| | Hydrogen | 4501 | 618 | — | — | — | — | — |
| | Methane | 1885 | 76918 | 30 | — | — | — | — |
| (See Table I) | Ethylene | — | 301 | 175612 | 24 | — | — | — |
| | Ethane | — | — | 94 | — | — | — | — |
| Composition of Heavy Naphtha (wt %) | Propylene | — | — | — | 84811 | 112 | — | — |
| | Propane | — | — | — | 45 | 36 | — | — |
| (See Table I) | 1,3-Butadiene | — | — | — | — | 33136 | 380 | — |
| | Other $C_4{}^s$ | — | — | — | — | 29990 | 591 | — |
| Steam to Hydrocarbon wt ratio - 0.6 | $C_5{}^s$ | — | — | — | — | 162 | 26972 | — |
| | Benzene | — | — | — | — | — | 42053 | — |

TABLE II-continued

| Gas Oil Feed (2.7925 billion lb/yr) | Other $C_4^s$ | — | — | — | — | — | 11722 | — |
|---|---|---|---|---|---|---|---|---|
| Properties: | Toluene | — | — | — | — | — | 22630 | — |
| | Other $C_7^s$ | — | — | — | — | — | 4609 | — |
| (See Table I) | Xylenes | — | — | — | — | — | 10207 | — |
| | Ethyl Benzene & Styrene | — | — | — | — | — | 12752 | — |
| Composition of Gas Oil (wt %) | Other $C_8^s$ | — | — | — | — | — | 1944 | — |
| | $C_9$ - 400° F. | — | — | — | — | — | 17941 | — |
| (See Table I) | Fuel Oil | — | — | — | — | — | — | 96807 |
| Steam to Hydrocarbon wt ratio - 0.8 | Total | 6387 | 77837 | 175736 | 84880 | 63436 | 151801 | 96807 |

COMPONENT YIELDS BASED ON A SINGLE PASS CONVERSION OF 100 PARTS BY WEIGHT FEED

| | |
|---|---|
| Hydrogen | 0.78 |
| Methane | 12.00 |
| Ethylene | 26.78 |
| Ethane | 0.01 |
| Propylene | 12.91 |
| Propane | 0.01 |
| 1,3-Butadiene | 5.13 |
| Other $C_4^s$ | 4.66 |
| $C_5^s$ | 4.13 |
| Benzene | 6.40 |
| Other $C_6^s$ | 1.79 |
| Toluene | 3.44 |
| Other $C_7^s$ | 0.70 |
| Xylenes | 1.55 |
| Ethyl Benzene & Styrene | 1.94 |
| Other $C_8^s$ | 0.30 |
| $C_9$ - 400° F. | 2.73 |
| Fuel Oil | 14.74 |
| Total | 100.00 |

TABLE III

| Number | 48 | 50 | 74 | 51 | 54 | 80 | 98 |
|---|---|---|---|---|---|---|---|
| Stream Component | Unsaturated $C_4$ Hydrocarbon Feed lb/hr | Hydrogen To Hydrogenation Reactor lb/hr | n-Butane Product lb/hr | Hydrogenation Reactor Effluent lb/hr | Reaction Mass lb/hr | Isobutane Rich Distillate lb/hr | Recycle Stream Into Tower 24 lb/hr |
| Hydrogen | — | 1197.3 | — | 241.5 | — | — | 19.82 |
| Methane | — | 502.4 | — | 502.4 | — | — | 11.6 |
| Pentane | — | — | — | 57.2 | — | — | — |
| 1,3-Butadiene | 165.2 | — | — | — | — | — | — |
| Butene-1 | 8898.4 | — | — | — | — | — | — |
| Isobutylene | 13390.6 | — | — | 269.3 | — | 269.3 | — |
| n-Butane | 3619.7 | — | 30218.9 | 17435.8 | — | 2074.75 | 14954.36 |
| iso-Butane | 1086.5 | — | 1590.2 | 14675.5 | — | 39419.77 | 26818.96 |
| cis-Butene-2 | 1688.4 | — | — | — | — | — | — |
| trans-Butene-2 | 2581.2 | — | — | — | — | — | — |
| Methyl Acetylene & Propadiene | 52.0 | — | — | — | — | — | — |
| Total | 31482 | 1699.7 | 31809.1 | 33181.7 | — | 41763.82 | 41804.74 |
| Temperature, °F. | 110 | 110 | 170 | 243 | — | 140 | 100 |
| Pressure, PSIG | 100 | 430 | 200 | 410 | — | 114 | 250 |
| Gallons/Minute | 114.5 | — | 117.8 | — | 2000 | 161.0 | 157.5 |

| Number | 102 | 86 | 92 | 104 | 72 | 100 |
|---|---|---|---|---|---|---|
| Stream Component | Recycled From Compressor 20 lb/hr | Effluent From Heat Exchanger 38 lb/hr | Feed Into Isomerization Reactor lb/hr | Hydrogen To Isomerization Reactor lb/hr | Purge Gas lb/hr | Stream From Vessel 36 Recycled From Isomerization Reactor lb/hr |
| Hydrogen | 158.8 | 151.12 | 160.62 | 29.32 | 261.32 | 131.1 |
| Methane | 44.8 | 44.8 | 44.8 | 11.6 | 514 | 33.2 |
| Propane | — | — | — | — | 57.2 | — |
| 1,3-Butadiene | — | — | — | — | — | — |
| Butene-1 | — | — | — | — | — | — |
| Isobutylene | — | — | 269.3 | — | — | — |
| n-Butane | 493.9 | 15448.42 | 2568.65 | — | — | 493.9 |
| iso-Butane | 1196.9 | 28015.8 | 40616.77 | — | 581 | 1196.9 |
| cis-Butene-2 | — | — | — | — | — | — |
| trans-butene-2 | — | — | — | — | — | — |
| Methyl Acetylene & Propadiene | — | — | — | — | — | — |

TABLE III-continued

| | | | | | | |
|---|---|---|---|---|---|---|
| Total | 1894.4 | 43660.14 | 43660.14 | 40.92 | 1413.52 | 1855.3 |
| Temperature, °F. | 160 | 180 | 460 | 110 | −30 | 100 |
| Pressure, PSIG | 315 | 250 | 300 | 430 | 110 | 200 |
| Gallons/Minute | — | — | — | — | — | — |

While we have fully described an embodiment of the foregoing invention, it is to be understood that this description is offered by way of illustration only. The range of adaptability of the process presented herein is contemplated to include many variations and adaptions of the subject matter within the scope of normal butane and ethylene production, and it is to be understood that this invention is to be limited only by the scope of the appended claims.

We claim:

1. A process of converting unsaturated $C_4$ hydrocarbons into normal butane which comprises:
   a. passing a stream consisting essentially of unsaturated $C_4$ hydrocarbons in contact with hydrogen in a hydrogenation zone to react said hydrogen and said unsaturated $C_4$ hydrocarbons to form a stream of normal butane and isobutane;
   b. discharging said normal butane and isobutane stream from said hydrogenation zone and introducing said discharged normal butane and isobutane stream into a separation zone to separate said normal butane from said isobutane;
   c. discharging and recovering said normal butane from said separation zone;
   d. passing said isobutane from said separation zone into an isomerization zone to convert a portion of said isobutane into normal butane so that a stream of normal butane and isobutane is produced; and
   e. thereafter returning said stream of normal butane and isobutane produced in said isomerization zone into said separation zone to separate and recover the normal butane produced in said isomerization zone.

2. A process according to claim 1 wherein said normal butane recovered in step (c) is introduced into a cracking zone of an ethylene production facility as a feedstock for the production of ethylene.

3. A process according to claim 1 wherein said stream of unsaturated $C_4$ hydrocarbons is a butene raffinate stream generated in a butadiene recovery unit.

4. A process according to claim 1 wherein said stream of unsaturated $C_4$ hydrocarbons is a butene raffinate stream generated in a butadiene recovery zone of an ethylene production facility.

5. A process according to claim 1 wherein said hydrogen introduced into said hydrogenation zone is obtained from a demethanization zone of an ethylene production facility.

6. A process according to claim 1 wherein heat is generated in said hydrogenation zone and said heat is utilized to heat a process stream in said separation zone.

7. A process according to claim 1 wherein said hydrogeneration zone comprises a hydrogenation reactor which is operated at a temperature of about 200° to about 450° F. and a pressure of about 100° to about 500 psig.

8. A process according to claim 7 wherein said hydrogenation reactor releases heat at a temperature of about 250° F., which heat is utilized to reboil the bottoms liquid of a separation tower in said separation zone.

9. A process according to claim 7 wherein said hydrogenation reactor releases heat at a temperature of about 250° F., which heat is utilized to preheat said isobutane introduced into said isomerization zone.

10. A process according to claim 8 wherein said separation tower is operated at overhead temperatures of from about 100° to about 200° F. and overhead pressures of from about 55 to about 240 psig.

11. A process according to claim 7 wherein a liquid phase catalyst is employed in said hydrogenation reactor.

12. A process according to claim 11 wherein said liquid phase catalyst is a soluble homogeneous liquid phase hydrogenation catalyst.

13. A process according to claim 11 wherein a liquid reaction mass is withdrawn from said hydrogenation reactor and said reaction mass is utilized to reboil the bottoms liquid of a separation tower in said separation zone.

14. A process according to claim 7 wherein a heterogeneous phase hydrogenation catalyst is employed in said hydrogenation reactor.

15. A process according to claim 14 wherein said heterogeneous phase catalyst contains a material selected from the group consisting of palladium, platinum, nickel and chromium.

16. A process according to claim 14 wherein reactor effluent is discharged from said hydrogenation reactor and said reactor effluent is utilized to reboil the bottoms liquid of a separation tower in said separation zone.

17. A process according to claim 14 wherein reactor effluent is discharged from said hydrogenation reactor and said reactor effluent is treated in a scrubbing zone to remove high molecular weight compounds from said reactor effluent.

18. A process according to claim 1 wherein heat is generated in said hydrogenation zone and said heat is utilized to supply heat to said isomerization zone.

19. A process according to claim 1 wherein said isomerization zone includes an isomerization reactor which utilizes an isomerization catalyst.

20. A process according to claim 19 wherein said isomerization reactor is operated at a temperature of about 250° to about 950° F. and a pressure of about 250 to 700 psig.

21. A process according to claim 19 wherein said isomerization catalyst contains a material selected from the group consisting of aluminum chloride, aluminum bromide, noble metals and non-noble metals.

22. A process according to claim 1 wherein a stream of hydrogen is introduced into a normal and isobutane stream entering an isomerization reactor in said isomerization zone.

23. A process according to claim 22 wherein said hydrogen introduced into said normal butane and isobutane stream entering said isomerization reactor in said isomerization zone is obtaining from a demethanization zone of an ethylene production facility.

24. A process according to claim 1 further comprising:

introducing a second stream of normal butane and isobutane into said separation zone to produce additional amounts of normal butane.

25. A process according to claim 1 further comprising:
introducing a second stream of normal and isobutane into said isomerization zone to produce additional amounts of normal butane.

26. A process according to claim 1 further comprising:
introducing a second stream of unsaturated $C_4$ hydrocarbons into said hydrogenation zone to produce additional amounts of normal butane.

27. A process according to claim 1 wherein a purge gas stream is withdrawn from said separation zone and said purge gas stream is introduced into a process stream of an ethylene production facility to separate and recover components of said purge gas stream.

28. A process according to claim 1 wherein said stream of unsaturated $C_4$ hydrocarbons comprises either:
(i) a stream of unsaturated $C_4$ hydrocarbons from an ethylene production facility;
(ii) a stream of unsaturated $C_4$ hydrocarbons from a butadiene extraction unit which unit derives its feed from an ethylene production facility, or
(iii) any mixture of (i) and (ii).

29. A process according to claim 28 wherein said stream of unsaturated $C_4$ hydrocarbons also contains unsaturated $C_4$ hydrocarbons from another source.

30. A process according to claim 19 wherein the inlet temperature of the isomerization reactor is from about 250° to about 950° F. and the inlet pressure is from about 250 to about 700 psig.

31. A process according to claim 19 wherein the outlet temperature of the isomerization reactor is from about 210° to about 910° F. and the outlet pressure is from about 210 to about 660 psig.

32. A process according to claim 19 wherein said isomerization catalyst contains a support or base carrier which is comprised of a material selected from the group consisting of alumina, alumina-silica, alumina-boria, Y-type zeolite and Mordenite.

33. A process according to claim 22 wherein a hydrogen containing stream is separated from said normal and isobutane stream recovered from said isomerization zone and said hydrogen containing stream is introduced into said hydrogenation zone as a part of the hydrogen feed into said hydrogenation zone.

34. In a process for the production of ethylene by the pyrolytic cracking of hydrocarbons in a cracking zone to produce a process stream of cracked gases, introducing said process stream of cracked gases into a rapid cooling zone to cool said gases, passing said cooled process stream of cracked gases into a quench prefractionation and compression zone to further cool and compress said gases and remove heavy hydrocarbons, passing said process stream of compressed cracked gases through a demethanization zone wherein methane is removed from said process stream and a stream of hydrogen is generated, thereafter, directing said process stream of compressed cracked gases through a recovery zone wherein ethylene is recovered and a stream of butene raffinate is formed, the improvement comprising the steps of:

a. introducing said stream of butene raffinate into a hydrogenation zone wherein said butene raffinate is passed in contact with said stream of hydrogen generated in said demethanization zone at temperatures of about 200° to about 450° F. and a pressure of about 100 to about 500 psig to form a stream consisting essentially of normal butane and isobutane;

b. discharging said stream of normal butane and isobutane from said hydrogenation zone and introducing said discharged normal butane and isobutane stream into a separation zone to separate said normal butane from said isobutane in a separation tower which is operated at overhead temperatures of from about 100° to about 200° F. and overhead pressures of from about 55 to about 240 psig;

c. discharging said normal butane from said separation zone and introducing said normal butane from said separation zone into said cracking zone as a feedback for the production of ethylene;

d. passing said isobutane from said separation zone into an isomerization zone wherein a portion of said isobutane is converted into normal butane in the presence of an isomerization catalyst to form a stream of normal butane and isobutane; and e. thereafter, returning said stream of normal butane and isobutane produced in said isomerization zone into said separation zone to separate the normal butane produced in said isomerization zone.

35. A process according to claim 34 wherein heat is generated in said hydrogenation zone which heat is utilized to separate said normal butane from said isobutane in said separation tower.

36. A process according to claim 34 wherein heat which is generated in said hydrogenation zone is utilized to preheat said isobutane entering said isomerization zone.

* * * * *